(12) United States Patent
Hausmanns et al.

(10) Patent No.: US 9,072,724 B2
(45) Date of Patent: Jul. 7, 2015

(54) COLLAGEN HYDROLYSATE FOR USE TO IMPROVE THE HEALTH OF HUMAN SKIN, HAIR AND/OR NAILS

(71) Applicant: GELITA AG, Eberbach (DE)

(72) Inventors: Stephan Hausmanns, Mannheim (DE); Monika Giesen-Wiese, Höchst (DE); Steffen Oesser, Glücksburg (DE)

(73) Assignee: GELITA AG, Eberbach (DE)

( * ) Notice: Subject to any disclaimer, the term of this patent is extended or adjusted under 35 U.S.C. 154(b) by 0 days.

(21) Appl. No.: 13/888,812

(22) Filed: May 7, 2013

(65) Prior Publication Data

US 2013/0252899 A1    Sep. 26, 2013

Related U.S. Application Data

(63) Continuation of application No. PCT/EP2011/067028, filed on Sep. 29, 2011.

(30) Foreign Application Priority Data

Nov. 15, 2010 (DE) .......................... 10 2010 060 564

(51) Int. Cl.
| | | |
|---|---|---|
| *A61K 38/39* | (2006.01) | |
| *A61K 47/48* | (2006.01) | |
| *A23J 1/02* | (2006.01) | |
| *A23J 1/04* | (2006.01) | |
| *A61K 38/17* | (2006.01) | |
| *C07K 1/00* | (2006.01) | |
| *C07K 14/00* | (2006.01) | |
| *C07K 16/00* | (2006.01) | |
| *C07K 17/00* | (2006.01) | |
| *A61K 8/65* | (2006.01) | |
| *A61Q 19/08* | (2006.01) | |
| *A23L 1/305* | (2006.01) | |
| *A61Q 3/00* | (2006.01) | |
| *A61Q 5/00* | (2006.01) | |

(52) U.S. Cl.
CPC . *A61K 38/39* (2013.01); *A61K 8/65* (2013.01); *A61Q 19/08* (2013.01); *A61Q 3/00* (2013.01); *A61Q 5/002* (2013.01); *A23L 1/3053* (2013.01)

(58) Field of Classification Search
CPC ........ A23L 1/3053; A61K 38/39; A61K 8/65; A61Q 19/08; A61Q 3/00; A61Q 5/002
See application file for complete search history.

(56) References Cited

U.S. PATENT DOCUMENTS

| | | | |
|---|---|---|---|
| 4,130,555 | A | 12/1978 | Ohtsuka et al. |
| 6,025,327 | A | 2/2000 | Alkayali |
| 2007/0293427 | A1 | 12/2007 | Vouland et al. |

FOREIGN PATENT DOCUMENTS

| | | |
|---|---|---|
| CN | 101518645 A | 9/2009 |
| DE | 42 44 418 A1 | 7/1993 |
| EP | 0 120 722 A1 | 10/1984 |
| FR | 2 900 155 A1 | 10/2007 |
| JP | 04-069 319 A | 3/1992 |
| JP | 2007-326 869 A | 12/2007 |

OTHER PUBLICATIONS

Saiga et al. Angiotensin I-Converting Enzyme-Inhibitory Peptides Obtained from Chicken Collagen Hydrolisae. J Agric Food Chem, 2008. vol. 56, pp. 9586-9591.*
Huo et al. Study on Enzymatic Hydrolysis of *Gadus morrhua* Skin Collagen and Molecular Weight Distribution of Hydrolysates. Agricultural Sciences in China, 2009. vol. 8, No. 6, pp. 723-729.*
Cohen et al. Small-Molecule Desorption/Ionization Mass Analysis in MALDI MS. A Practical Guide to Instrumentation, Methods and Applications. 2007, pp. 299-337, accessed online at http://masspec.scripps.edu/publications/public_pdf/118_EGo_art.pdf on Oct. 6, 2014.*
Wenzel et al. Comparison of Sensitivity and Saturation of MALDI-TOF Detectors for High Mass Ions. ASMS Proceedings, 2006, 2 pages, accessed online at http://www.covalx.com/files/scientificreports/ASMS06-Wenzel.pdf on Oct. 6, 2014.*
Huo, J. et al., "Study on Enzymatic Hydrolysis of *Gadus morrhua* Skin Collagen and Molecular Weight Distribution of Hydrolysates", *ScienceDirect*, No. 8(6), 2009, pp. 723-729.
International Search Report, Application No. PCT/EP2011/067028, mailed May 25, 2012.
International Preliminary Report on Patentability, Application No. PCT/EP2011/067028, mailed May 25, 2012.
"The ideal protein for a healthy lifestyle," Company Brochure. *Rousselot S.A.S.*, France, Feb. 2009. http://www.parmentier.de/gelatin/kollagen.pdf, Retrieved on Jan. 30, 2011.
"Wellness in our daily Life," Naticol 1000. Naticol 4000.*Weishardt International NA*, Quebec, Canada, Mar. 2008. http://www.weishardt.com/doc/brochurenaticol.pdf, Retrieved on Jan. 31, 2011.

(Continued)

*Primary Examiner* — Marcela M Cordero Garcia
(74) *Attorney, Agent, or Firm* — Leydig, Voit & Mater, Ltd.

(57) ABSTRACT

The invention relates to a collagen hydrolysate for use to improve the health of human skin, hair and/or nails, at least 90% by weight of the collagen hydrolysate having a molecular weight of less than 3,500 Da and the collagen hydrolysate comprising at least four characteristic peptides with a molecular weight between 600 and 1,200 Da.

18 Claims, 7 Drawing Sheets

(56) References Cited

OTHER PUBLICATIONS

Figure 1A:
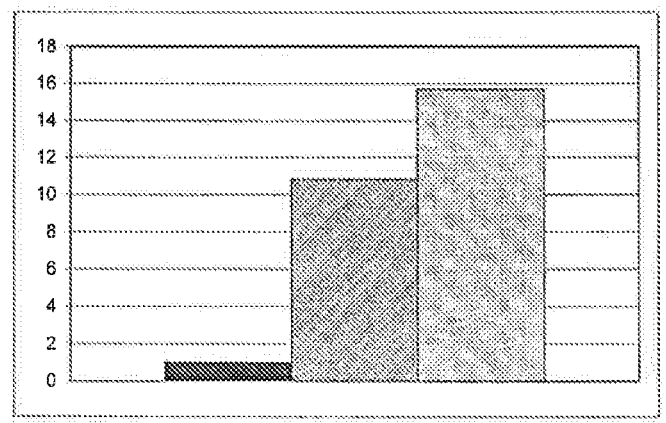

English translation of International Preliminary Report on Patentability, Appln. No. PCT/EP2011/067028, mailed on May 25, 2013.

Fujimura, T. et al.; "Epidermal change can alter mechanical properties of hairless mouse skin topically treated with 1alpha, 25-dihydroxyvitamin D(3)," *J. Dermatol. Sci.*, 24(2), 105-11, Nov. 2000.

German Search Report, Appln. No. DE 10 2010 060 564.6, mailed on Feb. 8, 2011.

Hara, M. et al., "Selectively reduced glycerol in skin of aquaporin-3-deficient mice may account for impaired skin hydration, elasticity, and barrier recovery," *J Biol Chem.*, 277(48), 46616-21, Sep. 2002.

Liang, J. et al.; "The protective effects of long-term oral administration of marine collagen hydrolysate from chum salmon on collagen matrix homeostasis in the chronological aged skin of Sprague-Dawley male rats," *J Food Sci.*, 75(8), H230-H238, Oct. 2010.

Nishimori, Y. et al.; "Degenerative alterations of dermal collagen fiber bundles in photodamaged human skin and UV-irradiated hairless mouse skin: possible effect on decreasing skin mechanical properties and appearance of wrinkles," *J Invest Dermatol.*, 117(6), 1458-63, Dec. 2001.

Tanaka, M. et al., "Effects of collagen peptide ingestion on UV-B-induced skin damage" *Biosci. Biotechnol. Biochem.*, 73(4), 930-2, Apr. 7, 2009.

Zague, V. "A new view concerning the effects of collagen hydrolysate intake on skin properties." *Arch Dermatol Res.*, 300(9),479-483, Oct. 2008.

\* cited by examiner

COLLAGEN HYDROLYSATE FOR USE TO IMPROVE THE HEALTH OF HUMAN SKIN, HAIR AND/OR NAILS

The present invention relates to a collagen hydrolysate for use to improve the health of human skin, hair and/or nails.

It has been known for some time that advantageous effects in relation to the health of the skin, but also the hair and/or nails in a human can be achieved by the oral intake of collagen hydrolysate (see, for example, Vivian Zague: "A new view concerning the effects of collagen hydrolysate intake on skin properties" in *Arch. Dermatol. Res.* 2008 (9) 479-483). An improvement in the health of the skin in this context is taken to mean every positive influence on the natural properties and functions of the skin, it being possible for these properties and functions to be impaired both as a consequence of ageing and also, additionally, by various negative environmental influences. An intake of collagen hydrolysate also has an advantageous effect on the properties of hair and/or nails.

The invention is based on the object of further increasing the positive effects of collagen hydrolysate on the health of skin, hair and/or nails and proposing a particularly effective collagen hydrolysate for this use.

The object is achieved according to the invention in the collagen hydrolysate of the type mentioned at the outset in that at least 90% by weight of the collagen hydrolysate has a molecular weight of less than 3,500 Da, and in that the collagen hydrolysate comprises at least four characteristic peptides with a molecular weight between 600 and 1,200 Da.

Collagen hydrolysates contain peptides with different chain lengths or molecular weights, which are produced during the cleavage of the protein chains of the collagen, it being possible for the molecular weight distributions of these peptides to differ significantly depending on the production conditions of the hydrolysate. It has now surprisingly been shown that a collagen hydrolysate with the aforementioned properties has a particularly advantageous effect on the health of the skin in various respects, i.e. exhibits significantly better results than in the previously used collagen hydrolysates that contain a substantially smaller proportion of low-molecular peptides and/or do not contain the characteristic peptides.

The molecular weight distribution of the collagen hydrolysate, on which the limit of at least 90% by weight below 3,500 Da is based, can be determined very precisely and reproducibly, for example by means of a gel permeation chromatography using a calibration standard of defined collagen fragments.

Preferably, at least 45% by weight of the collagen hydrolysate has a molecular weight of less than 1,500 Da, i.e. a certain proportion of the peptides of the collagen hydrolysate is particularly short-chained. It has been shown that very pronounced effects on the health of the skin can be achieved by such particularly low-molecular proportions, which are only contained in a substantially smaller quantity in currently used collagen hydrolysates.

The mean molecular weight (weight-average $M_w$) of the collagen hydrolysate used according to the invention is typically in the range of about 1,700 to about 2,300 Da.

The presence of the characteristic peptides of the collagen hydrolysate, which interestingly substantially contribute to its effectiveness, can, in particular, be determined by means of MALDI mass spectroscopy, the characteristic peptides in the mass spectrum occurring as peaks. The at least four characteristic peptides in a molecular weight distribution determined by means of MALDI mass spectroscopy preferably have at least twice the intensity, more preferably at least four times the intensity, in comparison to their surroundings.

In a preferred embodiment of the invention, the collagen hydrolysate comprises a peptide between 620 and 690 Da, a peptide between 790 and 860 Da, a peptide between 980 and 1,050 Da and a peptide between 1,175 and 1,245 Da. These peptides distinguish the collagen hydrolysate according to the invention in a characteristic manner from known collagen hydrolysates.

The collagen hydrolysate can additionally also have characteristic peptides between 1,500 and 3,500 Da, which are also a distinguishing feature from collagen hydrolysates according to the prior art.

The collagen hydrolysate preferably has a proportion of hydroxyproline of 12% by weight or more. The amino acid hydroxyproline formed by a post-translational hydroxylation of proline occurs exclusively in collagen, so a high proportion of hydroxyproline in the collagen hydrolysate is a measure of the substantial absence of other connective tissue proteins (for example elastin and proteoglycans), the fragments of which, depending on the production method, can also be contained in certain quantities in collagen hydrolysates.

It is favourable if the collagen hydrolysate is produced by enzymatic hydrolysis of gelatine. Gelatine comprises denatured collagen and is obtained by means of various methods known to the person skilled in the art from the connective tissue or from the bones of various types of animals. In the scope of the present invention, the gelatine used as the starting material for the collagen hydrolysate is preferably obtained from the skin of mammals, in particular from pigskin or bovine split, although the use of gelatine from poultry is not ruled out.

The enzymatic hydrolysis of the gelatine generally takes place by means of at least one endoprotease, it being preferred in the scope of the invention to use a plurality of endoproteases (i.e. at least two different endoproteases), to thereby correspondingly influence the amino acid profile of the resulting collagen hydrolysate and to increase the positive effect of the hydrolysate on the health of the skin, hair and/or nails.

According to a preferred embodiment of the invention, the collagen hydrolysate is produced by the consecutive action of at least two endoproteases with a different specificity, in particular of at least two different metalloproteases and/or serine proteases, i.e. of proteases, which cleave the amino acid sequence of the collagen molecules before or after specific amino acids, in each case. The metalloproteases and/or serine proteases are advantageously enzymes from the microorganisms *Bacillus subtilis*, *Bacillus licheniformis*, *Bacillus amyloliquefaciens*, *Aspergillus oryzae* and *Aspergillus melleus*.

By selecting suitable endoproteases, not only can the characteristic molecular weight distribution of the collagen hydrolysate be obtained, but the type of amino acids on the termini of the peptides contained in the hydrolysate is influenced. In this respect, it is, for example, preferred, if at least 50% of the N-terminal amino acids of the collagen hydrolysate are hydrophobic amino acids, in particular alanine, leucine and isoleucine.

The invention in particular also relates to the use of the collagen hydrolysate to stimulate the biosynthesis of extracellular matrix proteins by skin cells. Skin cells comprise, in particular, fibroblasts, which, inter alia, synthesise collagen (primarily of Type I), elastin and proteoglycans. The formation of these proteins in an adequate quantity is decisive for the building or the regeneration of the extracellular matrix of the skin, which is in turn substantially decisive for the properties of the skin, such as tonicity and elasticity and its moisture balance.

The skin cells also include keratinocytes, which are responsible both for the cornification of the outermost skin layer and also the formation of hair and nails. Thus, a stimulation of these cells by the collagen hydrolysate used according to the invention can bring about an improvement in the barrier function of the skin and the health of the hair and/or nails.

An important aspect of the invention relates to the use of the collagen hydrolysate to increase the tonicity of the skin and/or to reduce the formation of wrinkles. These properties of the skin generally worsen as a result of ageing and as a consequence of environmental influences, such as, for example, UV radiation or toxic substances. As, in particular, the matrix proteins collagen and elastin are responsible for the tonicity and elasticity of the skin, their augmented synthesis, which is stimulated to a particular extent by the collagen hydrolysate used according to the invention, can counteract these effects and the health of the skin can be significantly improved.

A further important aspect of the invention relates to the use of the collagen hydrolysate to increase the moisture content of the skin. A substantial contribution to the ability of the skin to bind adequate quantities of moisture is made by the proteoglycans (for example versican, biglycan and decorin) contained in the extracellular matrix, the synthesis of which is also shown to be stimulated by the collagen hydrolysate used according to the invention. The moisture content of the skin can also be reduced by damaging environmental influences such as UV radiation, the moisture loss frequently being accompanied by less suppleness, chapping and excessive cornification of the skin.

A further aspect of the invention relates to the use of the collagen hydrolysate to improve the barrier function of the skin. A substantial role in this barrier function is played by the so-called CE-proteins ("Cornified Envelope" proteins), inter alia involucrin, loricrin and filaggrin, the biosynthesis of which is demonstrably stimulated by the low-molecular collagen hydrolysate. Therefore, due to the use according to the invention of collagen hydrolysate, the reduction in the moisture loss, the barrier function and the natural protection of the skin against pathogenic germs and toxic substances are improved.

The use according to the invention of the collagen hydrolysate additionally also leads to an anti-oxidative effect in the region of the skin, so the frequency of DNA damage (mutations), for example owing to UV radiation or mutagenic substances, can be reduced. Such mutations are one of the causes of premature ageing of cells and thus promote ageing symptoms of the skin (reduction in the tonicity, formation of wrinkles, etc.), so this process can be inhibited by the use according to the invention.

According to a preferred embodiment of the invention, the collagen hydrolysate is provided for oral intake. In the case of oral intake, a more effective transportation of the collagen hydrolysate is often produced by way of the blood circulation to the site where it is effective, i.e. in particular to the skin cells, than is the case with a topical application. In addition, this form of application is generally linked with substantially less effort for the user.

The collagen hydrolysate is preferably used as a nutritional supplement. The collagen hydrolysate is generally used here to improve the health of the skin in the sense of a general health provision or else a cosmetic application; such nutritional supplements can be called "nutraceuticals" or "nutricosmetics". However, use of the collagen hydrolysate to treat a clinical disorder is also possible in the scope of the present invention, for example when atopic dermatitis is present, in which the patients have an increased tendency to dry, chapped skin.

The nutritional supplement can be offered in almost any form, for example in the form of tablets, capsules, sugar-coated tablets, pastilles or else a solution (for example in individual ampoules or in drinks).

The collagen hydrolysate can, alternatively, also be contained in food products or luxury food products, for example in confectionary or in an instant powder for providing drinks. The hydrolysate can thus be taken in by the user without additional effort in the course of normal nutrition (so-called "functional food"). In this context, it is particularly advantageous if the collagen hydrolysate is substantially neutral with respect to taste.

It is favourable if a daily intake of about 1.5 to 5 g, preferably about 2 to 3 g, more preferably about 2.3 to 2.7 g of the collagen hydrolysate is provided. It has been shown that the health of the skin can already be noticeably improved within a few weeks by the oral intake of this quantity of hydrolysate.

A further preferred embodiment of the invention relates to the topical application of the collagen hydrolysate, i.e. the application in the form of cosmetic products for application to the skin, the hair and/or the nails. The collagen hydrolysate may, in this case, be contained, in particular, in a cream, an ointment, a lotion or a gel. It is also favourable if the collagen hydrolysate is added to a body care product, such as, for example, a shower gel or a hair shampoo, for example in a quantity of about 5 to 10% by weight.

Figure 1B:
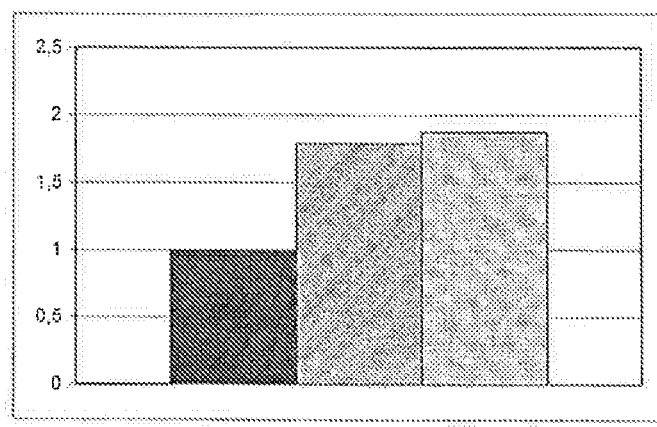
Figure 1C:
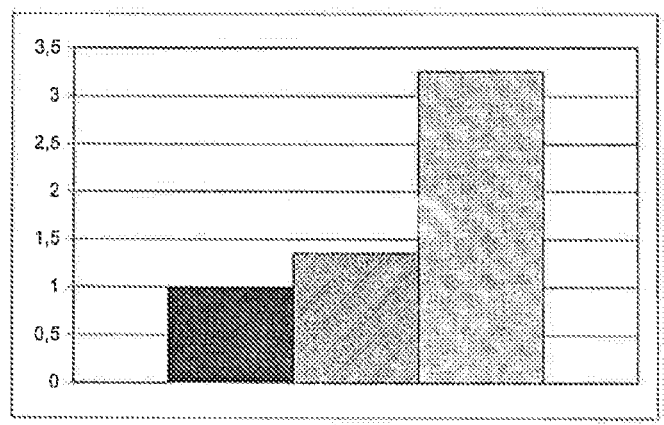
Figure 2A:
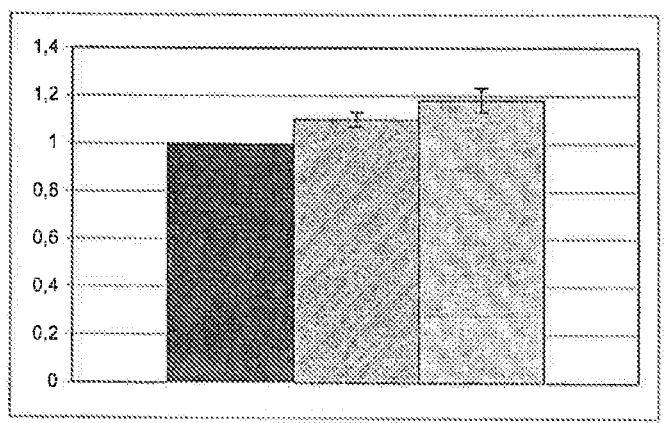
Figure 2B:
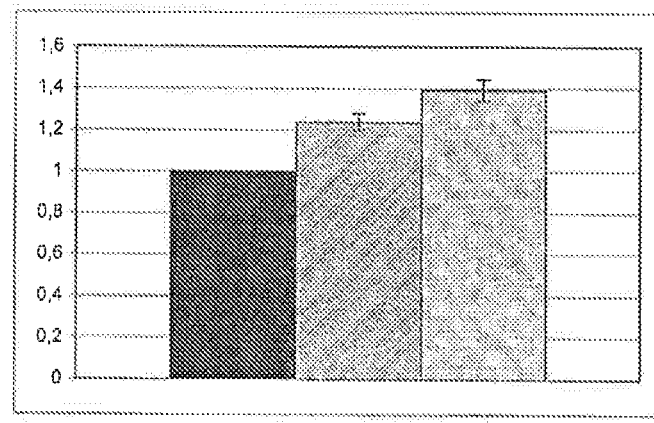
Figure 3:
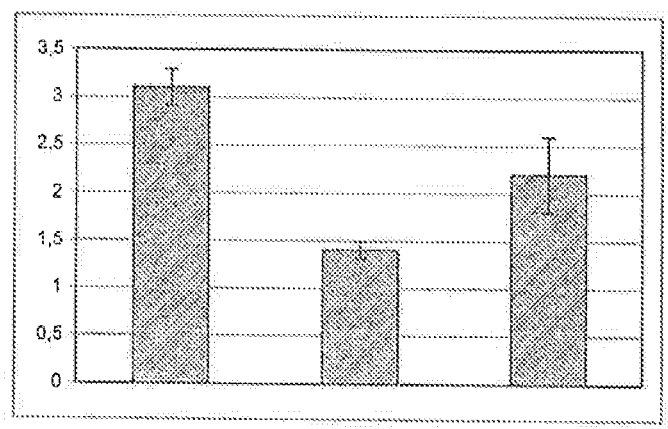
Figure 4A:
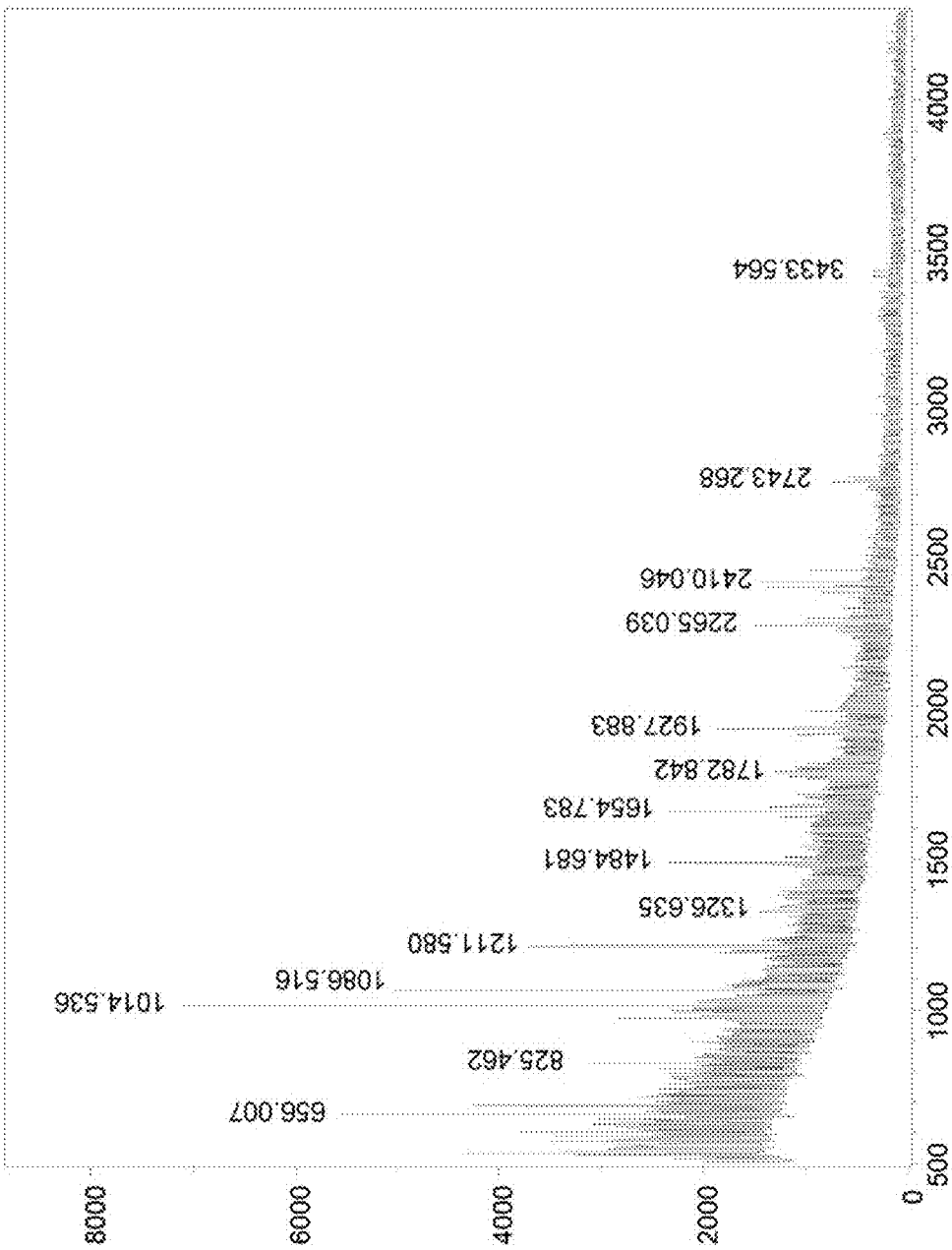
Figure 4B:
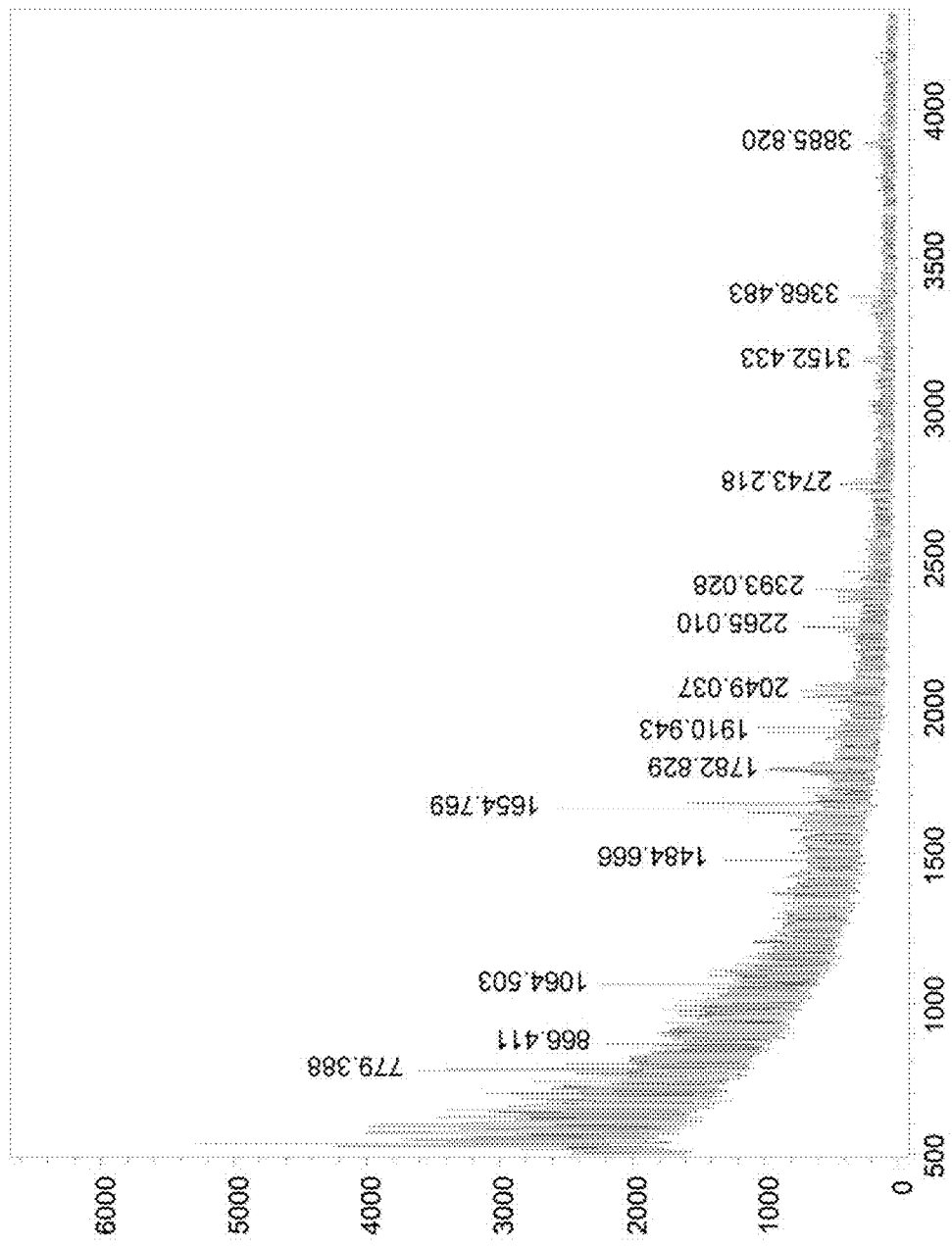
Figure 4C:
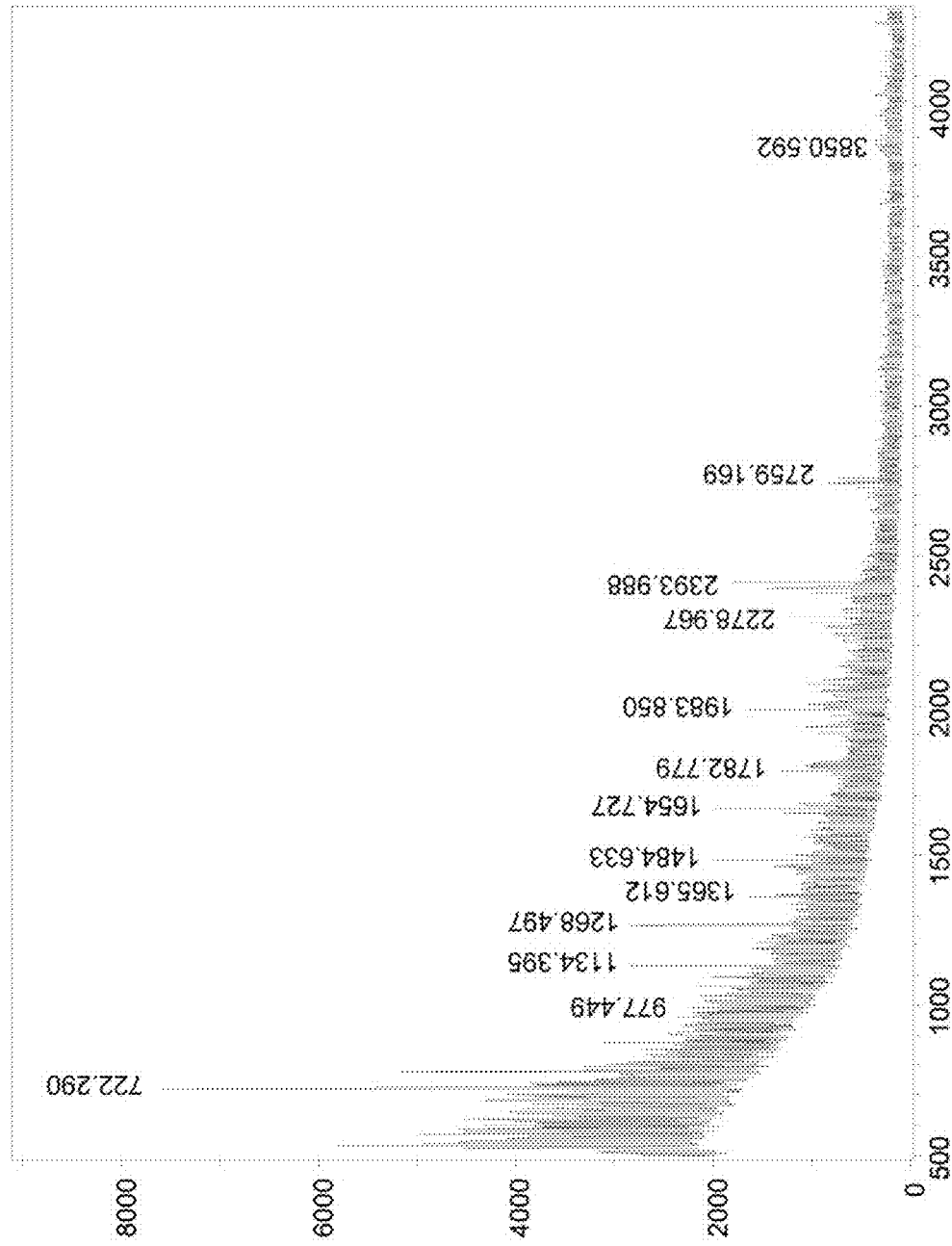

This and further advantages of the invention will be described in more detail with the aid of the following examples with reference to the Figures, in which, in detail:

FIGS. 1A to 1C: show graphs relating to the stimulation of the synthesis of Type I collagen, biglycan or versican;

FIGS. 2A and 2B: show graphs relating to the increase in the skin moisture in hairless mice;

FIG. 3: shows a graph relating to the stimulation of the synthesis of CE-proteins;

FIGS. 4A to 4C: show MALDI mass spectra for various collagen hydrolysates; and

Figure 5A:
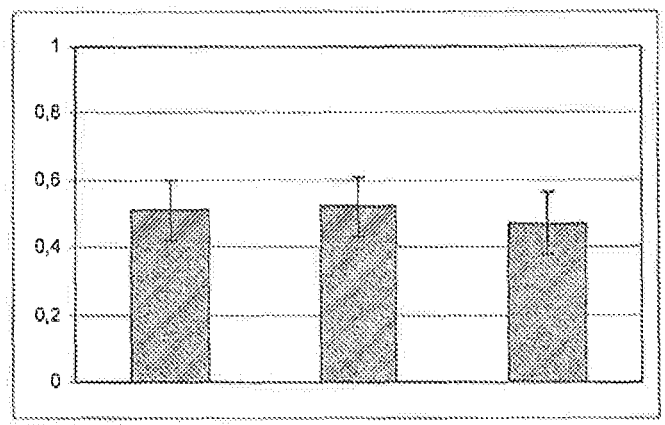
Figure 5B:
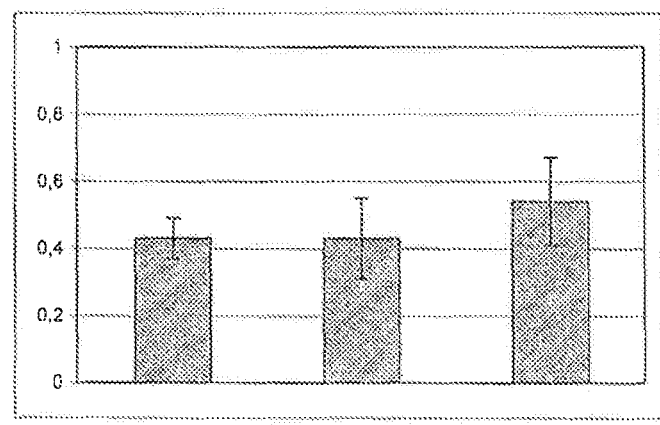

FIGS. 5A and 5B: show graphs relating to the stimulation of the synthesis of Type I collagen, decorin and versican.

EXAMPLES

1. Production and Properties of the Collagen Hydrolysate

To produce a collagen hydrolysate according to the invention, an aqueous solution of a pigskin gelatine (Type A, 200 to 250 g Bloom) with a concentration of 20 to 40% by weight (dry substance) is used as the starting material. The gelatine is enzymatically hydrolysed by the consecutive action of two different endoproteases of microbial origin for 120 to 180 min at 50 to 60° C., an endoprotease of *Bacillus subtilis* or of *Bacillus amyloliquefaciens* being used as the first enzyme and an endoprotease of *Bacillus licheniformis* being used as the second enzyme. The enzymes are then thermally inactivated and the solution is spray-dried.

The molecular weight distribution of the resulting collagen hydrolysate can be determined by means of gel permeation chromatography using the following parameters:

Stationary phase: TSK 2000 SW XL (Tosoh Bioscience GmbH)

Mobile phase: 0.4 mol/l sodium dihydrogen phosphate pH 5.3

Flow rate: 0.5 ml/min

Calibration standard: defined collagen Type I fragments (FILK, Freiberg)

Detection: UV-detector Knauer K-2501 at 214 nm

The determination produced a molecular weight distribution of the collagen hydrolysate according to the invention (called low-molecular hydrolysate below) according to the following Table 1. For comparison, the molecular weight distribution of a commercially available collagen hydrolysate, which was determined by the same method, is also given in Table 1 (called a high-molecular hydrolysate below):

TABLE 1

| MV-range | low-mol. hydrolysate | high-mol. hydrolysate |
|---|---|---|
| >7,500 Da | <5% by weight | <10% by weight |
| 3,500-7,500 Da | about 12-18% by weight | about 25-35% by weight |
| 1,500-3,500 Da | about 25-31% by weight | about 29-35% by weight |
| 500-1,500 Da | about 40-46% by weight | about 24-30% by weight |
| <500 Da | about 5-10% by weight | about 2-5% by weight |

The hydroxyproline content of this low-molecular hydrolysate is about 12 to 13% by weight and, after oxidation with chloramine-T and conversion with p-dimethylaminobenzaldehyde, can be determined photometrically. More than 50% of the N-terminal amino acids of the hydrolysate are hydrophobic amino acids, in particular alanine, leucine and isoleucine.

2. Stimulation of the Synthesis of Extracellular Matrix Proteins

The stimulation of the synthesis of collagen (Type I) and of the proteoglycans biglycan and versican was investigated in vitro on human dermal fibroblasts (skin cells). For this purpose, the cells were incubated for 24 hours with, in each case, 0.5 mg/ml of the low-molecular or the high-molecular hydrolysate and then the expression of collagen-RNA, biglycan-RNA and versican-RNA was determined by means of real time PCR and evaluated semiquantitatively (based on a control without hydrolysate).

The results are shown as a bar chart for Type I collagen in FIG. 1A, in FIG. 1B for biglycan and in FIG. 1C for versican, the graphs in each case showing the mean value of at least 18 measurements. The RNA-expression relative to the control (=1) is plotted on the abscissa. The left-hand filled bar in each case stands for the control, the central hatched bar for the high-molecular hydrolysate (as a comparison) and the right-hand dotted bar for the low-molecular hydrolysate (according to the invention).

It is shown that the synthesis of all three matrix proteins is stimulated by the two collagen hydrolysates, the positive effect of the low-molecular hydrolysate in each case being more pronounced than that of the high-molecular hydrolysate. In the case of the collagen, which, apart from elastin, has the main responsibility for the toncity and elasticity of the skin, and in the case of versican, which plays an important role in the moisture balance of the skin, the increased effect of the low-molecular hydrolysate is particularly clear.

3. Increase in the Moisture Content of the Skin

The influencing of the skin moisture by collagen hydrolysate was directly investigated on hairless mice. Hairless mice are an established model system, which is often used in dermatological investigations, and the knowledge obtained therefrom can in principle be transferred to human skin (see, for example, T. Fujimura et al.; *J. Dermatol. Sci.* 2000 (24) 105-411 and Y. Nishimori et al.; *J. Invest, Dermatol* 2001 (117) 1458-1463).

The animals were fed daily for a period of three weeks with 150 µg collagen hydrolysate per kg bodyweight and the control group instead received BSA. At the same time, all the animals received a weekly UV-B-radiation dose of 18 mJ/cm$^2$ skin surface, by which the skin moisture was impaired.

The moisture content of the skin was measured after one week and after three weeks using a Corneometer CM 825 (producer: Courage & Khazaka). The measuring principle is based here on the change in the capacitance of a measuring capacitor by the dielectric constant of the water bound in the upper skin layers, which differs significantly from the dielectric constant of most other materials.

The results are shown as bar graphs for the measurement after one week in FIG. 2A and for the measurement after three weeks in FIG. 2B, the graphs in each case showing the mean value and the standard error of 7 measurements. The skin moisture relative to the control (=1) is plotted on the abscissa. The left-hand filled bar in each case stands for the control, the central hatched bar for the high-molecular hydrolysate (as a comparison) and the right-hand dotted bar for the low-molecular hydrolysate (according to the invention).

It is shown that the increase in the skin moisture is in each case greater due to the low-molecular hydrolysate both after one week and after three weeks than due to the high-molecular hydrolysate. This is further evidence for the particular effectiveness of the hydrolysate used according to the invention in the improvement of the health of the skin.

4. Stimulation of the Synthesis of CE-Proteins

So-called "cornified envelope"-proteins play an important role in the barrier function of the skin against the penetration of pathogenic germs and toxic substances. The synthesis of the CE-proteins involucrin, loricrin and filaggrin was determined in hairless mice, which were fed beforehand for five weeks daily with 150 µg collagen hydrolysate per kg bodyweight (as described above). The quantification of the proteins relative to a control group (feeding with BSA) took place by means of SDS polyacrylamide gel electrophoresis and western blot with specific antibodies after extraction of the proteins from the skin.

The results are shown as a bar graph in FIG. 3, the graph in each case showing the mean value and the standard error from 7 measurements. The quantity of the CE-proteins after feeding with the low-molecular hydrolysate relative to the control (=1) is plotted on the abscissa. The left-hand bar stands for involucrin, the central bar for loricrin and the right-hand bar for filaggrin.

It is shown that the synthesis of all the three CE-proteins investigated is stimulated by the oral intake of the collagen hydrolysate used according to the invention, in the case of involucrin even by more than three times.

5. Anti-Oxidative Effect of the Collagen Hydrolysate

The anti-oxidative effect of the low-molecular collagen hydrolysate was determined in a cell-free system by means of malondialdehyde assay.

It was shown here that the formation of reactive oxygen species is reduced by the collagen hydrolysate by on average about 7%. The frequency of DNA damage can thus be reduced in the region of the skin, so ageing symptoms can be counteracted by the use according to the invention.

6. Analysis of the Molecular Weight Distribution in Means of MALDI-MS

The low-molecular collagen hydrolysate according to the invention, produced in accordance with Example 1, which has a mean molecular weight of about 2,000 Da (hydrolysate A below), was compared to two commercially obtainable collagen hydrolysates with a mean molecular weight of about 2,100 Da (hydrolysate B below) and about 2,900 Da (hydrolysate C below).

The precise molecular weight distributions of these three hydrolysates were analysed by means of MALDI mass spectroscopy (MALDI-MS). For this purpose, the samples were adjusted in 0.1% trifluoroacetic acid to a final concentration of 10 µg/µl and then purified using µ$C_{18}$-material. The samples were prepared with an HCCA matrix on a MALDI target and the mass spectra determined using an Ultraflex-III-TOF/TOF mass spectrometer (producer: Bruker Daltonics).

FIGS. 4A to 4C show the corresponding mass spectra or molecular weight distributions of the collagen hydrolysates A, B or C, the molecular weight or the mass number being plotted on the ordinate and the intensity being plotted on the abscissa. A comparison of the three spectra shows that the hydrolysate A according to the invention comprises the following characteristic peptides according to Table 2, the corresponding peaks having twice to four times the intensity in comparison to their surroundings:

TABLE 2

| |
| --- |
| about 656 Da |
| about 825 Da |
| about 1,014 Da |
| about 1,211 Da |
| about 1,927 Da |
| about 2,410 Da |
| about 3,433 Da |

In particular, the four peptides between 600 and 1,500 Da have no equivalents in the two commercial hydrolysates B and C, and are therefore particularly characteristic of the hydrolysate A.

7. Stimulation of the Synthesis of Extracellular Matrix Proteins

The stimulation of the synthesis of collagen (Type I) and the proteoglycans decorin and versican was investigated in vitro on human dermal fibroblasts (skin cells). For this, the cells were incubated for 24 hours with, in each case, 0.5 mg/ml of the hydrolysates A, B or C and the expression of collagen-RNA, decorin-RNA and versican-RNA was then determined by means of real time PCR and evaluated semi-quantitatively. Decorin plays an important role in the formation of collagen fibres in the skin.

The results are shown as bar graphs for the hydrolysate B in FIG. 5A and for the hydrolysate C in FIG. 5B, the RNA-expression being plotted in each case on the abscissa in the case of the commercial hydrolysates B or C relative to the RNA-expression in the hydrolysate A according to the invention (=1). The left-hand bar in each case stands for the Type I collagen, the central bar for decorin and the right-hand bar for versican. The mean value of at least 7 measurements is shown in each case as well as the standard error.

Interestingly, the data show that in all three matrix proteins, in comparison to the hydrolysate A, a significantly lower stimulation of the RNA-synthesis takes place due to the two hydrolysates B and C, the mean molecular weight of which is only slightly higher. The characteristic peptides of the hydrolysate A therefore appear to play a decisive role in its advantageous effect.

8. Exemplary Formulations for Food (Supplementing) Products and Cosmetics

Some exemplary formulations for the use of the collagen hydrolysate according to the invention are given below, which can obviously be modified in diverse ways:

Capsettes (Nutritional Supplements)

| | |
| --- | --- |
| Glycerine | 53.67% by weight |
| Collagen hydrolysate | 21.95% by weight |
| Gelatine | 10.08% by weight |
| Guar gum | 6.00% by weight |
| Lecithin | 5.00% by weight |
| Citric acid | 2.00% by weight |
| Flavouring (cassis) | 0.50% by weight |
| Orange oil | 0.50% by weight |
| Acesulfame K | 0.30% by weight |

Chocolate

| | |
| --- | --- |
| Cocoa paste | 51.0% by weight |
| Sucrose | 22.4% by weight |
| Cocoa butter | 16.6% by weight |
| Collagen hydrolysate | 10.0% by weight |

Drink

| | |
| --- | --- |
| Water | 63.00% by weight |
| *Aloe Vera* concentrate | 31.00% by weight |
| Collagen hydrolysate | 4.00% by weight |
| Sucrose | 1.50% by weight |
| Citric add | 0.26% by weight |
| Flavourings and colourants | 0.24% by weight |
| Sucralose | 0.0031% by weight |

Hair Shampoo

| | |
| --- | --- |
| Water | 58.8% by weight |
| Sodium laureth-11 carboxylate | 18.0% by weight |
| Coco amido propyl betaine | 9.0% by weight |
| Collagen hydrolysate | 6.0% by weight |
| PEG-6 caprylic/capric glycerides | 3.0% by weight |
| PEG-150 Distearate | 2.5% by weight |
| Laureth-7 | 2.0% by weight |
| Potassium sorbate | 0.5% by weight |
| Perfume | 0.2% by weight |

The invention claimed is:

1. A collagen hydrolysate for use to improve the health of human skin, hair and/or nails,
   wherein the collagen hydrolysate is derived from mammals or poultry,
   wherein the collagen hydrolysate is produced by the consecutive action of at least two metalloproteases and/or serine proteases with a different specificity,
   wherein at least 90% by weight of the collagen hydrolysate has a molecular weight of less than 3,500 Da,
   wherein the collagen hydrolysate comprises at least four characteristic peptides with a molecular weight between 600 and 1,200 Da, and
   wherein the at least four characteristic peptides, in a molecular weight distribution determined by MALDI mass spectroscopy, have an intensity of at least twice the intensity of their surroundings, the MALDI mass spectroscopy being carried out by adjusting a sample of the collagen hydrolysate in 0.1% trifluoroacetic acid to a final concentration of 10 μg/μl, purifying the adjusted sample using μC$_{18}$-material, preparing the sample with an alpha-cyano-4-hydroxycinnamic acid (HCCA) matrix on a MALDI target, and determining a mass spectrum of the sample using a TOF/TOF mass spectrometer.

2. The collagen hydrolysate according to claim 1, wherein at least 45% by weight of the collagen hydrolysate has a molecular weight of less than 1,500 Da.

3. A collagen hydrolysate for use to improve the health of human skin, hair and/or nails,
  wherein the collagen hydrolysate is derived from mammals or poultry,
  wherein the collagen hydrolysate is produced by the consecutive action of at least two metalloproteases and/or serine proteases with a different specificity,
  wherein at least 90% by weight of the collagen hydrolysate has a molecular weight of less than 3,500 Da,
  wherein the collagen hydrolysate comprises at least four characteristic peptides, the at least four characteristic peptides comprising a peptide having a molecular weight of between 620 and 690 Da, a peptide having a molecular weight of between 790 and 860 Da, a peptide having a molecular weight of between 980 and 1,050 Da and a peptide having a molecular weight of between 1,175 and 1,245 Da, and
  wherein the at least four characteristic peptides, in a molecular weight distribution determined by MALDI mass spectroscopy, have an intensity of at least twice the intensity of their surroundings, the MALDI mass spectroscopy being carried out by adjusting a sample of the collagen hydrolysate in 0.1% trifluoroacetic acid to a final concentration of 10 μg/μl, purifying the adjusted sample using μC$_{18}$-material, preparing the sample with an alpha-cyano-4-hydroxycinnamic acid (HCCA) matrix on a MALDI target, and determining a mass spectrum of the sample using a TOF/TOF mass spectrometer.

4. The collagen hydrolysate according to claim 1,
  wherein the collagen hydrolysate comprises further characteristic peptides, each peptide having a molecular weight between 1,500 and 3,500 Da, and
  wherein the further characteristic peptides, in a molecular weight distribution determined by MALDI mass spectroscopy, have an intensity of at least twice the intensity of their surroundings, the MALDI mass spectroscopy being carried out by adjusting a sample of the collagen hydrolysate OA % trifluoroacetic acid to a final concentration of 10 μg/μl, purifying the adjusted sample using μC$_{18}$-material, preparing the sample with a HCCA matrix on a MALDI target, and determining a mass spectrum of the sample using a TOF/TOF mass spectrometer.

5. The collagen hydrolysate according to claim 1, wherein the collagen hydrolysate has a proportion of hydroxyproline of 12% by weight or more.

6. The collagen hydrolysate according to claim 1, wherein the collagen hydrolysate is produced by enzymatic hydrolysis of gelatine.

7. The collagen hydrolysate according to claim 1, wherein the metalloprotcases and/or serine proteases are selected from enzymes from the microorganisms *Bacillus subtilis, Bacillus licheniformis, Bacillus amyloliquefaciens, Aspergillus oryzae* and *Aspergillus melleus.*

8. The collagen hydrolysate according to claim 1, wherein at least 50% of the N-terminal amino acids of the collagen hydrolysate are hydrophobic amino acids.

9. The collagen hydrolysate according to claim 1 for use to stimulate the biosynthesis of extracellular matrix proteins by skin cells.

10. The collagen hydrolysate according to claim 1 for use to increase the tonicity of the skin and/or to reduce the formation of wrinkles.

11. The collagen hydrolysate according to claim 1 for use to increase the moisture content of the skin.

12. The collagen hydrolysate according to claim for use to improve the barrier function of the skin.

13. The collagen hydrolysate according to claim 1, wherein the collagen hydrolysate is provided for oral intake.

14. The collagen hydrolysate according to claim 13, wherein the collagen hydrolysate is a nutritional supplement.

15. The collagen hydrolysate according to claim 13, wherein the collagen hydrolysate is contained in a food product or luxury food product.

16. The collagen hydrolysate according to claim 13, wherein a daily intake of about 1.5 to 5 g of the collagen hydrolysate is provided.

17. The collagen hydrolysate according to claim 1, wherein the collagen hydrolysate is provided for topical application.

18. The collagen hydrolysate according to claim 17, wherein the collagen hydrolysate is contained in a cream, an ointment, a lotion, a gel or a shampoo.

* * * * *